(12) United States Patent
Teoh et al.

(10) Patent No.: US 8,226,660 B2
(45) Date of Patent: *Jul. 24, 2012

(54) VASO-OCCLUSIVE COILS WITH NON-OVERLAPPING SECTIONS

(75) Inventors: Clifford Teoh, Los Altos, CA (US); Michael P. Wallace, Pleasanton, CA (US)

(73) Assignees: Stryker Corporation, Kalamazoo, MI (US); Stryker NV Operations Limited, Dublin (IE)

( * ) Notice: Subject to any disclaimer, the term of this patent is extended or adjusted under 35 U.S.C. 154(b) by 819 days.

This patent is subject to a terminal disclaimer.

(21) Appl. No.: 12/353,477

(22) Filed: Jan. 14, 2009

(65) Prior Publication Data

US 2009/0125054 A1    May 14, 2009

Related U.S. Application Data

(63) Continuation of application No. 10/791,092, filed on Mar. 1, 2004, now Pat. No. 7,488,332.

(51) Int. Cl.
*A61B 17/24* (2006.01)
(52) U.S. Cl. ....................................................... 606/113
(58) Field of Classification Search .................. 606/113, 606/114, 127, 151, 157, 159, 200
See application file for complete search history.

(56) References Cited

U.S. PATENT DOCUMENTS

| | | |
|---|---|---|
| 4,994,069 A | 2/1991 | Ritchart et al. |
| 5,226,911 A | 7/1993 | Chee et al. |
| 5,476,472 A | 12/1995 | Dormandy, Jr. et al. |
| 5,582,619 A | 12/1996 | Ken |
| 5,639,277 A | 6/1997 | Mariant et al. |
| 5,645,558 A | 7/1997 | Horton |
| 5,690,666 A | 11/1997 | Berenstein et al. |
| 5,749,891 A | 5/1998 | Ken et al. |
| 5,766,160 A | 6/1998 | Samson et al. |
| 5,853,418 A | 12/1998 | Ken et al. |
| 5,911,731 A | 6/1999 | Pham et al. |
| 5,951,539 A | 9/1999 | Nita et al. |
| 5,957,948 A | 9/1999 | Mariant |
| 6,004,338 A | 12/1999 | Ken et al. |

(Continued)

FOREIGN PATENT DOCUMENTS

WO    WO 0193937    12/2001

OTHER PUBLICATIONS

PCT International Search Report for PCT/US2005/004538, Applicant Boston Scientific Scimed, Inc., Forms PCT/ISA/210 and 220, dated May 27, 2005 (6 pages).

(Continued)

*Primary Examiner* — Kevin T Truong
(74) *Attorney, Agent, or Firm* — Vista IP Law Group LLP

(57) ABSTRACT

A vaso-occlusive implant has a primary helical-coil shape that defines a primary axis and a three-dimensional secondary shape. The secondary shape includes a substantially helical section and a second section having a plurality of non-overlapping loops or loop sections. Each loop defines a plane that is oriented at an angle from about 30-150 degrees relative to a plane defined by an immediately preceding or immediately succeeding loop along the primary axis. The coil sections or loops can be generally circular loops or other smooth shapes.

14 Claims, 4 Drawing Sheets

U.S. PATENT DOCUMENTS

| | | | |
|---|---|---|---|
| 6,010,517 | A | 1/2000 | Baccaro |
| 6,013,084 | A | 1/2000 | Ken et al. |
| 6,024,765 | A | 2/2000 | Wallace et al. |
| 6,136,015 | A | 10/2000 | Kurz et al. |
| 6,179,857 | B1 | 1/2001 | Diaz et al. |
| 6,231,586 | B1 | 5/2001 | Mariant |
| 6,254,592 | B1 | 7/2001 | Samson et al. |
| 6,306,153 | B1 | 10/2001 | Kurz et al. |
| 6,322,576 | B1 | 11/2001 | Wallace et al. |
| 6,371,972 | B1 | 4/2002 | Wallace et al. |
| 6,544,275 | B1 | 4/2003 | Teoh |
| 6,551,340 | B1 | 4/2003 | Konya et al. |
| 6,605,101 | B1 | 8/2003 | Schaefer et al. |
| 6,616,617 | B1 | 9/2003 | Ferrera et al. |
| 6,623,493 | B2 | 9/2003 | Wallace et al. |
| 6,635,069 | B1 | 10/2003 | Teoh et al. |
| 6,660,020 | B2 | 12/2003 | Wallace et al. |
| 6,929,654 | B2 | 8/2005 | Teoh et al. |
| 7,029,486 | B2 | 4/2006 | Schaefer et al. |
| 7,488,332 | B2 * | 2/2009 | Teoh et al. .................... 606/113 |
| 2002/0019647 | A1 | 2/2002 | Wallace et al. |
| 2002/0107534 | A1 | 8/2002 | Schaefer et al. |
| 2003/0018356 | A1 | 1/2003 | Schaefer et al. |
| 2003/0120302 | A1 | 6/2003 | Minck, Jr. et al. |

OTHER PUBLICATIONS

PCT Written Opinion of the International Search Authority for PCT/US2005/004538, Applicant Boston Scientific Scimed, Inc., Form PCT/ISA/237, dated May 27, 2005 (5 pages).

* cited by examiner

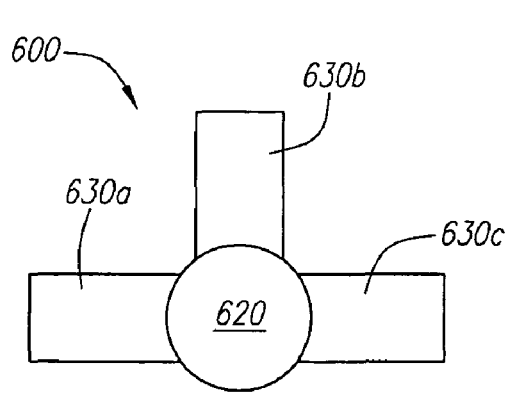
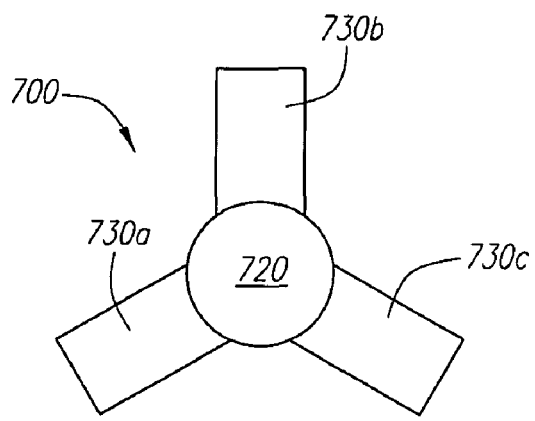
*FIG. 6*  *FIG. 7*
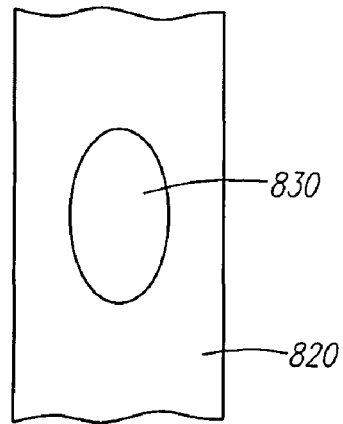
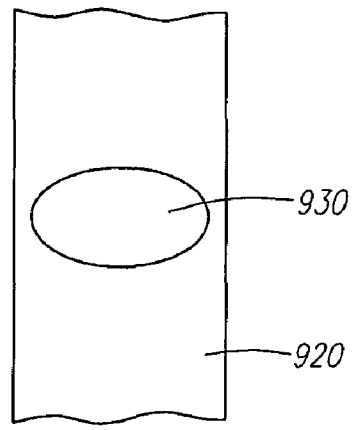
*FIG. 8*  *FIG. 9*

VASO-OCCLUSIVE COILS WITH NON-OVERLAPPING SECTIONS

RELATED APPLICATION DATA

This application is a continuation application of co-pending U.S. patent application Ser. No. 10/791,092, filed Mar. 1, 2004, the priority of which is claimed under 35 U.S.C. §120, and the contents of which are incorporated herein by reference in their entirety, as though set forth in full.

FIELD OF INVENTION

The present invention relates generally to vaso-occlusive devices and, more particularly, to vaso-occlusive implants having a helical coil primary shape and a secondary shape that includes non-overlapping sections.

BACKGROUND

Vaso-occlusive devices are implants that are placed in cavities within a patient's vasculature, e.g., within an aneurysm located in the vasculature of the brain. The devices are typically implanted using a delivery catheter that is advanced endoluminally to the treatment site.

An example of a well-known vaso-occlusive device has an elongated helically-wound "primary shape" when constrained within a delivery catheter, and a three-dimensional "secondary" shape once deployed from the catheter and left, more or less, unconstrained in the implantation site. Because of the helical primary shape, these devices are generally referred to as vaso-occlusive devices. The coils are typically made of a very soft and flexible metal, e.g., a platinum alloy. Depending on the size and/or shape of the aneurysm, one or more occlusive coils may be implanted in order to reduce the risk of the aneurysm growing and/or rupturing. The vaso-occlusive coils may also promote embolization of the aneurysm.

To manufacture the vaso-occlusive coils, a wire comprising the coil material is first wound around a small diameter, primary mandrel and heated to produce the helical primary shape. The primary shape coil is then wrapped around a larger diameter secondary mandrel, which is heated to set the secondary shape into the primary shape coil.

One disadvantage of this process is that the secondary windings (which are larger loops formed by the elongate primary coil) often overlap one another as the primary shape coil is wound onto or around the secondary mandrel. In particular, kinks and abrupt bends can form in the coil as a result of overlapping winding around the secondary mandrel, and can become "programmed" into the secondary shape of the coil during heat treatment. These kinks and bends can increase frictional resistance of the coil as it is advanced through a delivery catheter, requiring greater force to deploy the coil into the aneurismal cavity. Kinks and bends can also cause problems in the event a coil that is partially deployed needs to be withdrawn from the body, as they can more readily snag other deployed coils at the site. Additionally, uneven or overlapping secondary windings can result in coils that impart greater stresses on aneurysm walls, increasing the chance the aneurysm wall can be damaged or burst.

SUMMARY

In accordance with one embodiment, a vaso-occlusive coil includes an elongate helical primary shape that defines a primary axis, and a three-dimensional secondary shape that includes a substantially helical first section and a second section. The second section includes a plurality of non-overlapping loops. Each loop defines a plane oriented at an angle from about thirty degrees to about one hundred fifty degrees relative to a plane defined by an immediately preceding or an immediately succeeding loop along the primary axis.

In accordance with another embodiment, a vaso-occlusive coil includes a substantially helical primary shape that defines a primary axis, and the primary shape is wound into a three-dimensional secondary shape. The secondary shape includes a substantially helical first section and a second section immediately following the first section along the primary axis. The second section includes a plurality of non-overlapping loops, including a first loop, a second loop immediately following the first loop along the primary axis, and a third loop immediately following the second loop along the primary axis. The first loop defines a plane oriented at an angle of at least about thirty degrees relative to a plane defined by the second loop. The second loop defines a plane oriented at an angle of at least about thirty degrees relative to a plane defined by the third loop.

Other aspects and features of the coils will become apparent from consideration of the following description taken in conjunction with the accompanying drawings.

BRIEF DESCRIPTION OF THE DRAWINGS

FIG. 6 illustrates a top view of an alternative mandrel configuration having three posts arranged in a "T" arrangement;

FIG. 7 illustrates a top view of another alternative mandrel configuration having three posts arranged in a generally triangular arrangement;

FIG. 8 illustrates a partial side view of an alternative mandrel configuration having an elliptically shaped position; and FIG. 9 illustrates a partial side view of another alternative mandrel configuration having an elliptically shaped post in a different orientation.

DETAILED DESCRIPTION OF THE ILLUSTRATED EMBODIMENTS

In the following description, reference is made to the accompanying drawings, which show by way of illustration specific embodiments. It is to be understood that other embodiments may also be utilized.

Generally, vaso-occlusive coils are manufactured by winding an elongate coil having a helical primary shape and defining a primary axis around a secondary mandrel. The secondary mandrel and wound primary shape coil are heated to program or set a three-dimensional secondary shape. The secondary shape includes a substantially helical first section and a second section that includes a plurality of non-overlapping loops. The coils also have smooth surfaces. Each loop defines a plane that is oriented at an angle (e.g. 30-150 degrees) relative to a plane defined by any immediately preceding or any succeeding loop along the primary axis.

Figure 1:
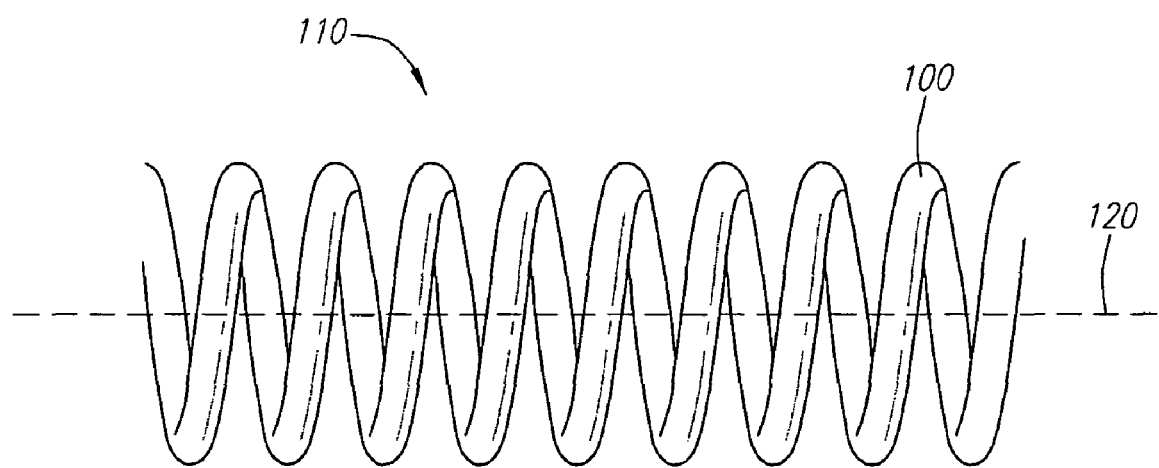
FIG. 1 generally illustrates a portion of coil material having an elongate helical primary shape that defines a primary axis.

More particularly, referring to FIG. 1, a wire or coil material 100 may be treated to assume a primary configuration or shape 110 that defines a primary axis 120. The primary coil shape 110 can be an elongate helical primary coil shape and can be established using known manufacturing methods. An axial length of the coil material 100 having the primary shape 110 may be, for example, between about one half and one hundred centimeters (0.5-100 cm), preferably between about two and forty centimeters (2-40 cm). The primary coil shape 110 may have between, for example, about ten and seventy five (10-75) turns per centimeter, and preferably between ten and forty (10-40) turns per centimeter. Persons of ordinary skill in the art will appreciate that various primary shapes 110 can be utilized, and that FIG. 1 is merely an illustrative example of various suitable shapes. The coil material 100 having the primary shape 110 can be treated further to assume a secondary shape.

Figure 2:
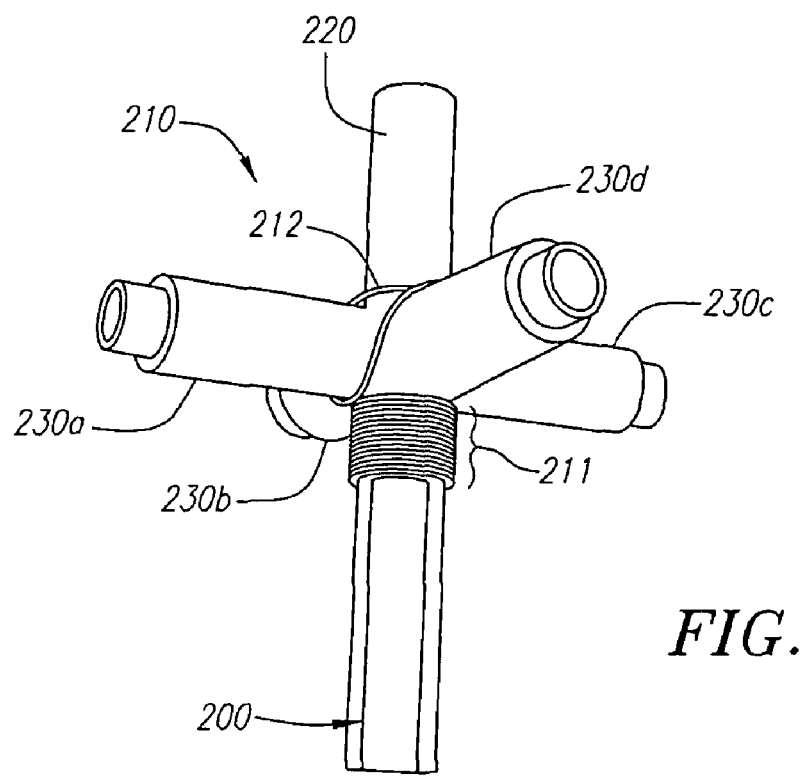
FIG. 2 illustrates an embodiment of a vaso-occlusive coil having a three-dimensional secondary shape that includes a substantially helical first section and a second section having a plurality of non-overlapping loops.

Referring to FIG. 2, after the primary shape 110 is set, the primary shape 110 coil may be wound around a secondary mandrel 200. The secondary mandrel 200 and the wound primary shape 110 coil are heat treated to form or program the primary shape 110 coil with the secondary shape 210.

Exemplary secondary mandrels 200 have a shaft 220 and one or more posts 230a-d (generally 230). A post 230 can extend from the shaft 220 at various angles and orientations. Persons of ordinary skill in the art will recognize that a "post" can be a "shaft" and that a "shaft" can be a "post" by re-positioning the secondary mandrel 200. For purposes of explanation and illustration, however, this specification refers to one or more "posts" 230 extending from a "shaft" 220 to establish a point of reference.

The secondary mandrel 200 may be formed from a variety of known materials capable of being heated during coil manufacturing, e.g., when the coil material or wire 100 is heat treated. Exemplary secondary mandrel 200 materials may include ceramic or other refractory materials including, but not limited to, alumina or zirconia.

The secondary mandrel 200 provides a support for winding the primary shape 110 coil and provides a specific secondary shape 210 when the secondary mandrel 200 and primary shape 110 coil are heated. For example, a primary shape 110 coil material made of a platinum/tungsten alloy and wound around the secondary mandrel 200 can be heated to about 1100.degree. F. for about 15-20 minutes to program or set the secondary shape 210.

Persons of ordinary skill in the art will recognize that heating temperatures and durations can vary with different materials. For example, heating temperatures and durations may be reduced when heating coil materials that are not made solely of metals but include one or more metallic components and non-metallic components, such as a meltable plastic.

The primary shape 110 coil can be wound around the shaft 220 and/or posts 230 one or more times for various degrees to form the secondary shape 210 coil. As shown in FIG. 2, the secondary shape 210 includes two sections—a substantially helical first section 211 and a second section 212. The substantially helical first section 211 is formed around the shaft 230. The second section 212 is formed above the first section 211 and around one or more posts 230. In the illustrated embodiment, the first section 211 is below the second section 212, but the first section 211 can also be formed above the second section 212.

The first section 211 includes a plurality of helical windings that are wrapped around the post 220. The second section 212 includes a plurality of non-overlapping loops. Each loop in the second section 212 defines a plane that is oriented at an angle (e.g., 30-150 degrees) relative to a plane defined by an immediately preceding or an immediately succeeding loop along the primary axis 120. The angles between the planes defined by the loops may vary depending on the number and arrangement of posts 220 of the secondary mandrel 200.

The primary shape 110 coil can be wrapped around the shaft 220 and/or one or more posts 230 for various degrees, e.g., less than about 360.degree., not more than 270.degree., and not more than 180.degree., depending on the required secondary coil shape 210 and number and arrangement of non-overlapping loops. After the secondary shape 210 has been set or programmed, it can be cut from the secondary mandrel 200. For example, the secondary shape 210 coil can be cut between the first helical section 211 and the second or loop section 212 or at other locations as necessary.

The sequence and pattern of non-overlapping primary shape 110 coil winding upon the secondary mandrel 200 can vary depending on the desired secondary shape 220. The primary shape 110 coil can be wound above, below, or both above and below a post 230 or a shaft 220 for various degrees. In some cases, the primary shape 110 coil may not be wound around the shaft 220 or only some of the posts 230.

Figure 3:
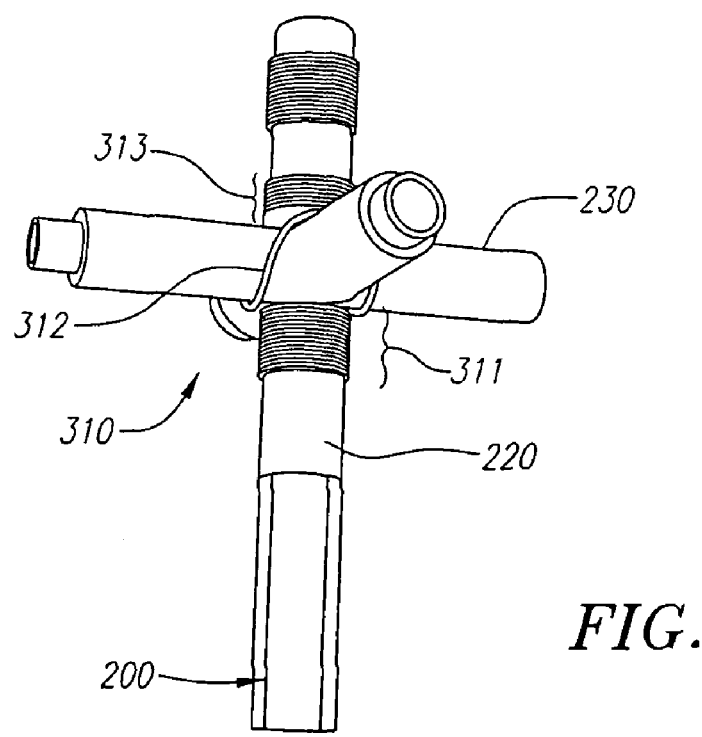
FIG. 3 illustrates an embodiment of a vaso-occlusive coil that includes a substantially helical first section, a second section having a plurality of non-overlapping loops, and a substantially helical third section.

FIG. 3 illustrates an alternative embodiment in which a secondary shape 310 includes three sections—a substantially helical first section 311 that is formed around the shaft 220, a second or middle section 312 that is formed above the first section 311 and around one or more posts 230, and a substantially helical third section 313 that is formed around the shaft 220 and above the second section 312. In this embodiment, the second or middle section 312 is formed around the posts 230 and between two substantially helical sections 311 and 313. The secondary shape 310 coil may be cut between the first and second sections 311 and 312 and between the second and third sections 312 and 313 or at other locations as necessary.

Figure 4:
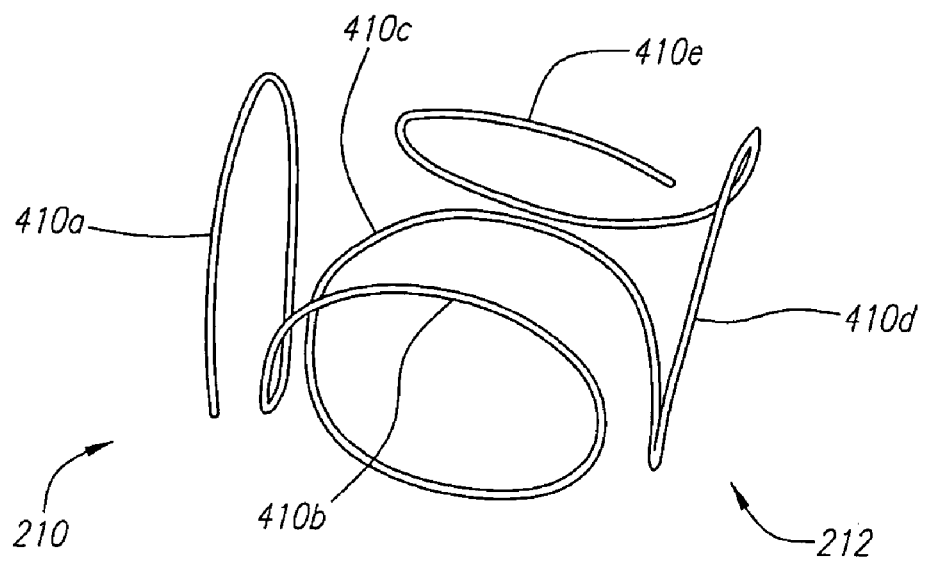
FIG. 4 illustrates an embodiment of a second or middle section of a vaso-occlusive coil that is removed from a mandrel and has a secondary shape.
Figure 5:
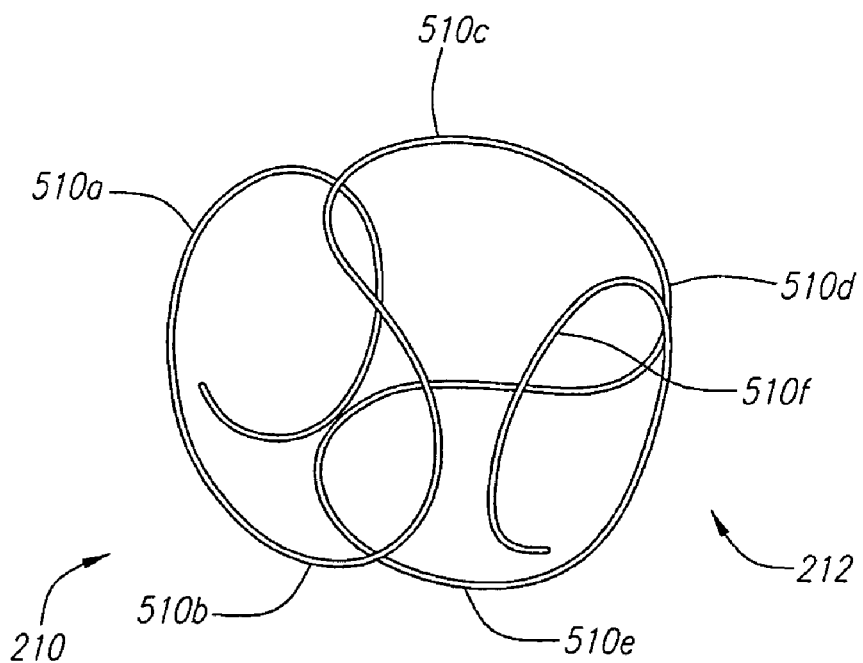
FIG. 5 illustrates another embodiment of a second or middle section of a vaso-occlusive coil that is removed from a mandrel and has a secondary shape.

FIGS. 4 and 5 illustrate exemplary loop structures of the second sections 212 and 312 (generally 212) of the secondary shapes 210 and 310 (generally 210). FIGS. 4 and 5, however, illustrate the second section 212 being separated from the one or more substantially helical sections. Further, considering that the coils are flexible under application of force, FIGS. 4 and 5 illustrate the coils in their initial, relaxed state in the absence of force.

Referring to FIG. 4, an, embodiment of a secondary shape 210 coil has a plurality non-overlapping loops that are generally smooth and free of pointed or kinked sections. In particular, this embodiment of a second section 212 includes five generally circular loops or loop sections 410a-e (generally 410) that define respective planes. A first loop 410a is directly connected to a second loop 410b. The loop 410b is directly connected to a third loop 410c. The loop 410c is directly connected to a fourth loop 410d. The loop 410d is directly connected to a fifth loop 410e. FIG. 5 illustrates an alternative second section 212 embodiment that includes six loops 510a-f that define respective planes. The loops in FIGS. 4 and 5 are shown as being approximately the same size and shape, however, other sizes and shapes can be utilized as necessary, for example, by using a shaft or post with other sizes and/or smooth shapes. Accordingly, the second coil sections 212 shown in FIGS. 4 and 5 are illustrative of other possible coils and winding patterns.

For example, various lengths of coil loops or loop sections 410 and 510 (generally 410) can be formed around an axis in the secondary configuration 210. A loop or loop section 410 of the coil sections 212 can extend around an axis for less than about three hundred sixty degrees (360.degree.). For example, the illustrated loops 410 are generally partial loops having coil winding for less than about 360.degree. Other degrees of winding can also be utilized, e.g., not more than about two hundred seventy degrees (270.degree.), and not more than one hundred eighty degrees (180.degree.). Indeed, different coil configurations can require different degrees of winding around the secondary mandrel 200 to form different loop or loop section configurations.

The relationship of one loop to other loops of the second coil section 212 can also vary depending on the particular non-overlapping winding pattern and secondary coil shape 210. For example, individual adjacent loops 410 can form planes that are oriented at various angles relative to one another, e.g., between about 30 and about 150 degrees. For example, an angle of about 30 degrees may result from using a larger number of winding posts, and larger angles may result from using fewer posts.

As shown in the illustrated embodiments, each plane defined by a loop 410 of the second coil section 212 is generally orthogonal to a plane defined by an adjacent loop. For example, in FIG. 4, a plane defined loop 410*a* (a side of the coil) is generally orthogonal to both a plane defined by loop 410*b* (a front of the coil) and a plane defined by loop 410*c* (a bottom of the coil). Similarly, planes defined by loops 410*a* and 410*b* are generally parallel to planes defined by loops 410*d* and 410*e*, respectively. Thus, depending on the winding and coil configuration, planes defined by various numbered loops can be generally parallel to opposite facing planes or be orthogonal to adjacent planes or at various angles depending on the particular configuration.

Persons of ordinary skill in the art will recognize that different numbers of loops can result in different coil shapes and can be made using different winding mechanisms. For example, a second coil section 212 can include different numbers of loops, e.g., less than about fifteen loops. FIG. 4 illustrates a second coil section 212 having five loops or loop sections, and FIG. 5 illustrates a second coil section having six loops or loop sections. Depending on the number of loops and/or the non-overlapping coil pattern, sections of the coil may or may not contact each other. Further, as shown in the illustrated embodiments, the ends of the coils can placed in various positions, e.g., in opposite loops, in adjacent loops, and in adjacent loops that are generally orthogonal to each other.

Persons of ordinary skill in the art will also recognize that a vaso-occlusive coil having non-overlapping coil sections can include various materials depending on the particular application. For example, the coil may be formed from metals, polymers, alloys, or composites thereof. Preferably, the coil includes a material that is compatible with magnetic resonance imaging.

In addition, the coil may include a radiopaque material, such as a metal, an alloy, or a polymer. Suitable metals and alloys for the wire defining the coil may include the platinum group metals, particularly platinum, rhodium, palladium, and rhenium, as well as tungsten, gold, silver, tantalum, and alloys of these metals. These materials have significant radiopacity, and their alloys may be tailored to have a blend of flexibility and stiffness for the coil. They are also generally biologically inert. A platinum/tungsten alloy may be most preferred, with ferrous material mixed with or carried by the alloy. Additional suitable materials are described in the Wallace et al. patent, incorporated by reference above.

Alternatively or in addition, the coil may be constructed from, or otherwise include radiolucent fibers or polymers (or metallic threads coated with radiolucent or radiopaque fibers), such as Dacron (polyester), polyglycolic acid, polylactic acid, fluoropolymers (polytetrafluoroethylene), Nylon (polyamide), and/or silk. When a polymer is used as the major component of the vaso-occlusive device, it may be filled with some amount of a radiopaque material, such as powdered tantalum, tungsten, bismuth oxide, barium sulfate, and the like. In addition, ferrous material, e.g., iron particles, filaments, and the like, may also be mixed with and/or embedded in the polymer.

When the coil is made from a platinum alloy or superelastic alloy, such as nitinol, or other materials, the diameter of the wire defining the coil may be between about 0.0005 and 0.006 inch (0.012-0.15 mm). The wire may be wound into a primary coil having a primary diameter between about 0.005 and 0.035 inch (0.125-0.625 mm), and preferably between about 0.010 and 0.018 inch (0.25-0.45 mm). Such wire may be of an appropriate diameter to provide sufficient hoop strength to hold the vaso-occlusive device in place within a chosen body cavity without distending the wall of the cavity and/or without moving substantially from the cavity as a result of the repetitive fluid pulsing experienced within the vascular system.

Additionally, various secondary mandrel 200 configurations can be used to produce different secondary shapes 210. For example, FIG. 6 illustrates a top view of a secondary mandrel 600 having three posts 630*a-c* arranged in a "T" shape around a shaft 620. FIG. 7 illustrates a top view of a secondary mandrel 700 having a group of three posts 730*a-c* having a triangular arrangement around a shaft 720. Thus, one group of posts can be arranged in square or orthogonal configuration (e.g., FIGS. 2-3), T configuration (e.g., FIG. 6), triangle configuration (e.g., FIG. 7) and various skewed or offset configurations as needed. Thus, although the Figures generally illustrate all of the posts being arranged transversely relative to the shaft, various non-transverse or offset orientations can also be used.

Other groups and numbers of groups of posts can also be utilized depending on the particular application. For example, two, five, six, seven, eight, nine, ten and other numbers of posts can be used as necessary. For purposes of explanation, and not limitation, this specification primarily refers to and illustrates secondary mandrels 200 having three or four posts extending from the shaft.

In addition to using various numbers of posts, other post configurations and orientations can be utilized for non-overlapping winding. Non-overlapping winding techniques can be utilized with posts that have smooth shapes other than generally circular shapes. For example, referring to FIGS. 8 and 9, smooth elliptical shaft 820, 920 and/or post 830, 930 shapes can be used. Other shapes, such as toroid, pear, dumbbell, and other smooth shapes can also be utilized as needed.

Additionally, different shaft 220 and post 230 sizes can be selected depending on, for example, the desired secondary coil shape 210 and the length of coil material that is to be wrapped around the secondary mandrel 200 in a non-overlapping manner. For example, one exemplary shaft/post is cylindrical and has diameters from about 1 mm to about 40 mm, preferably between 2 mm to about 20 mm. Other post and shaft diameters and sizes can be utilized depending on the particular application and device to be made.

In use, the resulting coil may be constrained in a primary configuration 110 and be biased to assume a three-dimensional secondary configuration 210 in a relaxed state. Thus, when the coil is not restricted by external forces or barriers, it may assume a relaxed, three-dimensional secondary shape 210. Additional information on suitable methods for manufacturing vaso-occlusive devices may be found in U.S. Pat. No. 6,322,576 to Wallace et al., the entire disclosure of which is incorporated by reference herein.

The coil assumes its primary (elongate helical coil) shape 110 when it is disposed within a catheter or other delivery device used to deliver the coil into a patient's body. The catheter is introduced into a patient's body, generally from a percutaneous entry site, e.g., into a peripheral artery, such as the femoral or carotid arteries (not shown), as is well known in the art. The catheter may be advanced over a guidewire or other rail previously placed within the patient's vasculature using known methods. The catheter may be advanced through the patient's vasculature until a distal end is disposed within a blood vessel adjacent an aneurysm.

Once the catheter is properly positioned, a vaso-occlusive coil in its primary configuration 110 may be advanced through a lumen of the catheter and into the aneurysm. As the vaso-occlusive coil is deployed and allowed to expand or relax, it assumes a three-dimensional secondary configuration 210, as previously discussed. Preferably, the secondary configuration is selected so that the vaso-occlusive coil substantially fills the aneurysm.

The catheter may be removed after the vaso-occlusive coil is fully deployed within the aneurysm, as is known in the art. Additional information on apparatus and methods that may be suitable for delivering a vaso-occlusive coil may be found in U.S. Pat. No. 4,994,069 to Ritchart et al., U.S. Pat. No. 6,623,493 to Wallace et al, and the Wallace et al. patent incorporated by reference above, the disclosures of which are incorporated by reference herein.

Those skilled in the art will appreciate that embodiments of coils having secondary shapes with non-overlapping sections, can be modified or altered for adaptation to other configurations and applications. For example, the secondary mandrel can include various other numbers, groups, and configurations of posts in planar, non-planar, transverse and non-transverse or angled arrangements. Various other post and shaft shapes and sizes can also be utilized. Different secondary coil shapes can be produced with these different secondary mandrel configurations to produce various non-overlapping loops or loop sections. Further, those skilled in the art will recognize that modifications, alterations, and substitutions can be made to the described embodiments.

What is claimed:

1. A vaso-occlusive coil having an elongate helical primary shape, the primary shape defining a primary axis, the primary shape being wound into a secondary shape comprising:
    a first, substantially helical first section having a plurality of complete loops;
    a second section having a plurality of complete, non-overlapping loops, each loop of the second section defining a plane oriented at an angle from about thirty degrees to about one hundred fifty degrees relative to a plane defined by any immediately preceding or any immediately succeeding loop along the primary axis; and
    a third, substantially helical section having a plurality of complete loops, wherein the second section is between the first and third sections along the primary axis.

2. The coil of claim 1, the respective loops of the first, second and third sections including generally circular loops.

3. The coil of claim 1, the respective loops of the first, second and third sections including generally elliptical loops.

4. The coil of claim 1, the respective loops of the secondary shape not contacting each other, absent a force being applied to the secondary shape.

5. The coil of claim 1, at least one loop of the second section defining a plane oriented generally orthogonal to a plane defined by any immediately preceding or succeeding loop of the second section along the primary axis.

6. The coil of claim 1, at least two loops of the second section defining respective planes disposed generally parallel to each other.

7. The coil of claim 1, at least one loop of the second section defining a plane disposed generally parallel to a plane defined by another loop of the second section.

8. The coil of claim 1, the respective loops of the second section being wound without contacting one another.

9. The coil of claim 1, a first loop of the section second defining a plane oriented generally orthogonal to a plane defined by a second loop of the second section, the second loop defining a plane oriented generally orthogonal to a plane defined by a third loop of the second section.

10. The coil of claim 9, the first loop defining a plane disposed generally parallel to a plane defined by the third loop.

11. The coil of claim 9, the second section further comprising a fourth loop immediately following the third loop along the primary axis, wherein the third loop defines a plane oriented at an angle of at least about thirty degrees relative to a plane defined by the fourth loop.

12. The coil of claim 11, the first loop defining a plane disposed generally parallel to a plane defined by either of the third or fourth loops.

13. The coil of claim 1, wherein respective planes defining first, second and third loops of the second section form a generally triangular configuration.

14. The coil of claim 1, the first and third sections of the secondary shape each having at least 10 complete loops.

* * * * *